United States Patent [19]

Ahmad et al.

[11] Patent Number: 5,204,260

[45] Date of Patent: * Apr. 20, 1993

[54] METHOD FOR MAKING BIOCONTROL AGENTS RHIZOSPHERE-COMPETENT

[76] Inventors: Syed J. Ahmad, Tahir Ahmadiyya Muslim High School, Mansakonko (L.R.D) The Gambia, South Africa; Ralph Baker, 1216 Southridge, Ft. Collins, Colo. 80521

[ * ] Notice: The portion of the term of this patent subsequent to Mar. 9, 2010 has been disclaimed.

[21] Appl. No.: 516,325

[22] Filed: Apr. 30, 1990

Related U.S. Application Data

[63] Continuation of Ser. No. 72,343, Jul. 10, 1987, abandoned.

[51] Int. Cl.$^5$ .................. C12N 1/14; C12N 15/00; A01N 63/00; A01C 1/06
[52] U.S. Cl. ........................ 435/254; 435/172.1; 435/945; 424/93 B; 424/93 Q; 47/57.6
[58] Field of Search ............... 435/172.1, 209, 254, 435/945; 424/93, 93 B, 93 Q; 47/58, 57.6

[56] References Cited

PUBLICATIONS

Cuskey S. M., Montenecourt, B. S., and Eveleigh, D. E. 1983. Screening for Cellulolytic, pp. 31–48 in Liquid Fuel Developments. Ed. D. L. Wise, pp. 31–47. CRC Press. Boca Raton, Fla. 210 pages.
Ghose, T. K. 1987. Measurement of Cellulose Activities. Pure and Appl. Chem. 59:257-268.
Sivan, A., and Harmon, G. E. 1991. Improved Rhizosphere Competence in a Protoplast Fusion Progeny of Trichoderma Harzianum. Journal of General Microbiology (1991), 137, 0000—0000.
Mendez-Castro and Alexander, Method for Establishing a Bacterial Inoculum on Corn Roots Eviron, Microbiol 45: 254-258 (1983).
Garrett S. D. Pathogenic Root Infected Fugi, Cambridge University Press (1970) Foster and Rovira & Cock, Ultrastructure of the Root Soil Interface, AM. Phytopath, Soc. St. Paul, Minn. (1983).
Ahmad and Baker, Competitive Saprophytic Ability and Celluloytic Activity of Rhizosphere-Competent Mutants of Trichoderma Harzionum; Phytopathology 77-358 (1987).
Ahmad and Baker, Rhizosphere-Competent in Trichoderma Harzanium Phytopathology (Feb. 1987), vol. 77: 182-189.
Foster et al, Ultrastructure of Root-Soil Interference, Am. Phytopath. Soc. St. Paul, Minn. (1983).
Lifshitz et al, *Decrease in Incidence of Rhizoctonia Pre-emergence Damping-Off* by Use of Integrated Chemical and Biological Controls, Plant Diseases, May 1985: 431.
Chang et al, *Increased Growth of Plants in Presence of Biological Control* Agent, Trichoderma Harzianum for Increased Plant Growth. Plant Dis. 70:145 (1986).
Papavizas, G. C. Trichoderma and Gliocladium: Biology, Ecology and Potential for Biocontrol Ann. Rev. Phytopathology 23: 23–54 at p. 35, 1985.
Papavizas, G. C., Survival of Trichoderma Harzianum in Soil and in Pea and Bean Rhizospheres: Ecology and Epidemiology, vol. 72, No. 1, 121–125 at p. 124 (1982).
Ahmad, J. S. & Baker, Ralph, Rhizosphere-Competence of Trichoderma Harzianum, Phytopathology 77: 182-189.

(List continued on next page.)

*Primary Examiner*—David T. Fox
*Attorney, Agent, or Firm*—Dorr, Carson, Sloan & Peterson

[57] ABSTRACT

Soilborne rhizosphere-incompetent biocontrol agents can be converted into rhizosphere-competent agents by exposing them to a mutagenic agent and then screening the exposed rhizosphere-incompetent agent for a strain showing increased cellulase production. The increased cellulase production characteristic serves to convert the originally rhizosphere-incompetent agent into one which is rhizosphere-competent. Seeds of plants to be protected against various diseases can then be treated with the rhizosphere-competent strain. The roots of the plant, as well as its original seed, are protected by biocontrol agents produced by the disclosed process.

1 Claim, 6 Drawing Sheets

OTHER PUBLICATIONS

Ahmad, J. S. & Baker, Ralph, Rhizosphere-Competence of Benomyl-Tolerant Mutants of Trichoderma spp., Can. J. Microbiol 34: 694–696 (1988).

Ahmad, J. S., & Baker, Ralph, Growth of Rhizosphere-Competent Mutants of Trichoderma Harzianum on Carbon, Can. J. Microbiol. 34: 807–814.

Baker, Ralph, "Induction of Rhizosphere Competence in Bioconatrol Fungus (1991) Trichoderma", Kluwer Academic Publishers, *The Rhizosphere and Plant Growth*, pp. 221–228.

Papavizas et al. 1982, Phytopathology 72(1): 126–132.

Mandels et al. 1971, Appl. Microbiol. 21(1): 152–154.

Ahmad et al. 1985, Phytopathology 75(11): 1302.

METHOD FOR MAKING BIOCONTROL AGENTS RHIZOSPHERE-COMPETENT

STATEMENT OF CO-PENDENCY

This patent application is a Continuation application of U.S. Pat. No. 72,343 entitled "Method For Making Biocontrol Agents Rhizosphere—Competent" filed Jul. 10, 1987, now abandoned.

BACKGROUND OF THE INVENTION

1. Field of the Invention

This invention generally relates to processes for identifying, developing and using new biotypes of soilborne biocontrol agents. More specifically it relates to mutagenic processes for converting soilborne rhizosphere-incompetent biocontrol agents into rhizosphere-competent biocontrol agents. The term "rhizosphere competence" has been employed to describe an attribute of rhizobia characterized by their consistent association with legume root nodules. Here, we use the term to describe the ability of a microorganism to grow and function in the developing rhizosphere.

2. Description of the Art

The protection of plants from infection by soilborne fungal and bacterial pathogens by use of antagonistic microorganisms is well known to the art. For example, it is known that various Trichoderma spp. such as *Trichoderma harzianum* Rifai act as biological control agents against certain plant diseases. Nonetheless, use of Trichoderma spp., as biocontrol agents has been rather limited. This is mainly because seed treatment with Trichoderma spp. generally does not provide continued protection for the emerging root system of the maturing plant. Such seed treatment does serve to reduce pre-emergence damping-off but the root system is left unprotected. It is generally believed that this failure to protect the root system is because Trichoderma spp. are not rhizosphere-competent, see for example, Papavizas, G. C., Phytopathology 72: 121–125 (1982) and Chao, W. L., et al., Phytopathology 76: 60–65 (1986). Therefore, a need clearly exists for more effective methods for inducing biocontrol agents to colonize a plant's developing root system as well as its spermosphere.

This need has been partially met in the realm of certain bacterial biocontrol agents; see for example, Mendez-Castro, F. A. and Alexander, M., Method for establishing a bacterial inoculum on corn roots, Appl. Eviron., Microbiol. 45: 254–258 (1983). A similar plant protection strategy has been applied to fungal biocontrol agents (Ahmad, J. S., and Baker, R., Induction of rhizosphere competence in *Trichoderma harzianum* (Abstr.) Phytopathology 75: 1302 (1985)). This work indicated that when benomyl-tolerant mutants of *Trichoderma harzianum* Rifai were applied to seeds, the roots became colonized. However, the reason or reasons as to why such mutants are rhizosphere-competent, were not apparent. It seemed that many of the results obtained from following this research strategy were inconsistent and/or in conflict with what was then known about rhizosphere-competence. For example, it should be noted that the Papavizas article previously cited discloses the use of benomyl tolerant isolates of *T. harzianum*, obtained by ultraviolet light irradiation to test for rhizosphere-competence of bean and pea seedlings. However, Applicants found that ultraviolet mutants, tolerant to benomyl were not rhizosphere competent. Moreover, reports by other workers (see for example, Garrett, S. D., Pathogenic root-infected fungi, Cambridge University Press (1970)) postulated the theory that the share of a substrate obtained by any particular fungal species is determined partly by its intrinsic competitive saprophytic ability and partly by the balance between its inoculum potential and that of competing species. This report also theorized that production of, and tolerance to, antibiotics is another important attribute of successful rhizosphere fungi.

All of these theories were however, to some degree, inconsistent with the results of Applicants' rhizosphere competence tests. For example, Applicants found that both the mutants and the wild types had the same population density when applied to seeds. Moreover, none of Applicants' mutant strains have antibiotic activity in vitro except for a routing factor seen in the hyphal cytoplasm, at microscopic levels affecting Pythium spp. In trying to reconcile these theoretical and/or evidentiary conflicts, as well as those relating to the nature of the plant root surfaces themselves (see Foster, R. C., Rovira, A. D., and Cock, T. W., Ultrastructure of the Root-Soil Interface. Am. Phytopath. Soc., St. Paul, Minn. (1983)), Applicants postulated that rhizosphere-competence was somehow related to a possible possession by the mutant strains of enzymes for cellulase degradation. The subsequent finding by the Applicants that a wide variety of rhizosphere-competent Trichoderma mutant strains do in fact possess increased cellulase degradation capabilities, is a key aspect of the overall teachings of this disclosure.

SUMMARY OF THE INVENTION

This invention provides a process whereby rhizosphere-incompetent biocontrol agents such as fungi and bacteria can be mutated into strains which are rhizosphere-competent. The disclosed process is particularly useful in producing rhizosphere-competent fungi capable of controlling diseases caused by Phythium spp., Sclerotuim spp., and *Rhizoctonia solani* in such varied plants as beans, maize, tomato, radish, cucumber, wheat, barley, lettuce, and carnations.

The mutation process of this invention can be induced by known means such as mutagenic chemicals. Applicants have found that N-methyl-N-nitro-N-nitrosoguanidine is a particularly useful mutagenic chemical in producing Trichoderma strains which possess the desired increased cellulase production characteristic. Other useful mutagenic agents would include, but not be limited to ultraviolet light and radiations.

The most straightforward means for producing and identifying biocontrol agents having the characteristic of increased cellulase production is to grow them in a nutrient medium where cellulase represents a major part of the agent's source of carbon, or more preferably its only source of carbon. Representative sources of carbon would include, but not be limited to carboxy methyl cellulase, cotton linters and solka floc.

The most effective cellulase producing strains of Trichoderma spp. thus far produced by Applicants have been deposited with the American Type Culture Collection, 12301 Parklawn Drive, Rockville, Md. 20852, under the following designations.

| Trichoderma spp. | Applicants' Designation |
|---|---|
| harzianum | T-12B |
| harzianum | T-95 |
| koningii | T-8-7 |

| Trichoderma spp. | Applicants' Designation |
|---|---|
| ATTC Designation | |
| 20835 | |
| 60850 | |
| 20836 | |

Other biocontrol agents which could be mutated by Applicants' methods to become rhizosphere-competent would include Fusarium spp., Penicillium spp., Mvrothecium spp., Chaetomium spp., and Glicladium spp.

In keeping with the provisions of the directive found on page 638, volume 886 of the Official Gazette of the United States Patent Office, progeny of each and every such strain will be made available during the pendency of this patent application to anyone determined by the Commissioner of Patents and Trademarks to be entitled thereto under 37 CFR §1.14 and 35 USC 12.2. All restrictions on the availability to the public of progeny of each and every such strain will be irrevocably removed upon the granting of a patent of which these strains are subject.

DESCRIPTION OF PREFERRED EMBODIMENTS

The competitive saprophytic ability (CSA) of strains of Trichoderma spp. was determined by the modified Cambridge method (sensu Garrett, S. D. Pathogenic root infection fungi. Cambridge University Press, London (1970)). Two rhizosphere-competent mutants of Tharzianum (T-95 and T-12B) had higher CSA indices than four rhizosphere-incompetent Trichoderma spp. and strains. CSA was directly correlated with rhizosphere competence. When the strains were grown for 6 days on Czapek Dox broth with cellobiose, carboxy methyl cellulose, or cotton linters as sole sources of carbon, mutants produced more cellulase than the wild types. The amount of cellulase produced by these strains was directly correlated with CSA and rhizosphere competence. Rhizosphere competence of the mutants, therefore, can be at least partially explained by their capacity to utilize cellulose substrates associated with the root. It should also be noted that the above noted Trichoderma are benomyl-tolerant.

METHODS

Tests for Rhizosphere Competence. Various methods have been employed to test rhizosphere competence. These were primarily based on a comparison of the numbers of cfu of microorganisms in the soil associated with roots to population densities in non-rhizosphere soil. The rhizosphere competence assay used in this research effort was developed to improve measurement in time and space of the activity of potential rhizosphere inhabitants. Certain criteria were demanded by the experimental questions to be examined. Quantitative analysis of population densities at each depth of root was necessary. No water was added during incubation obviating the possibility of propagules being washed into the rhizosphere. To test whether the agent introduced from a seed into the rhizosphere could compete under typical ecological condition, raw soil was used. Therefore, the system allowed rhizosphere competence to be measured on the basis of cfu/mg or g of rhizosphere soil as a function of root depth.

The nature and quantity of root exudates have been analyzed in the past in axenic systems by use of perfusion and filter paper absorption techniques. Since such analyses often are obtained under gnotobiotic conditions, it is difficult to extrapolate such findings into the ecological conditions present in the rhizospheres of plants growing in raw soil. To overcome this objection, bioassays relating relative magnitudes of microbial population densities in the rhizosphere compared with non-rhizosphere soil were developed, the R/S ratio. Such analyses are subjected to many variables and, at best, provide only a relative gross assay of the activity of the total biomass about the root. The rhizosphere competence assay provided a quantitative measurement of a specific rhizosphere-competent microorganism at the root tip where exudates are in relatively high concentration. In more mature portions of the root, however, interpretations based on population densities are confounded by maturation of the agent resulting in propagule production, various interaction leading to auto- or heterolysis, or changes in characteristics of substrates provided by senile tissues of the root. Nevertheless, the rhizosphere competence assay provides the best bioassay yet developed for the rhizosphere nutrient at root tips. It has potential for use in a wide variety of experimental problems related to ecological and nutritional interactions in the rhizosphere.

Several species of Trichoderma were tested for rhizosphere competence by coating the seed with each isolate and following population densities of the fungus to a root depth of 8 cm. No species grew to greater depth than 2 cm. This confirms the conclusions of other workers that Trichoderma spp. are not rhizosphere-competent.

Additional evidence for rhizosphere competence of strain T-95 was obtained by microscopic observations comparing the length of hyphae on root originating from seeds coated with or without conidia of the fungus. Of course, it was not possible to identify with certainty the hyphae of T-95; however, the total length of hyphae observed was relatively similar to the cfu obtained by use of the rhizosphere competence assay.

Roots were essential for colonization below the site (seed) where the strains of Trichoderma were applied.

The wild type was recovered at low densities to a 4-cm depth; mutants were recovered at all depths of rhizosphere sand when applied to seed. Neither the wild type nor a mutant was recovered below the glass beads.

Our particular rhizosphere-competence assays were conducted as follows. Polypropylene centrifuge tubes (28.6 by 103.6 mm) were sliced longitudinally into two halves. Each half was filled with moistened soil ($-0.03$ bars) and pre-incubated for 48 hours in plastic bags. One treated seed was placed on the half-tube 1 cm below the rim. The unseeded half-tube was placed on the first half and secured with rubber bands. Tubes were completely randomized and lots in portions of six each were placed vertically in 10 cm diameter plastic pots. Soil, previously moistened to $-0.03$ bars and of the same pH as in the tubes, was added to the pots so that the length of the tube was surrounded by the soil, with the top 1 cm of each tube uncovered. No water was added to the tubes or the pots after seed were sown. Pots were covered with plastic bags to maintain constant matric potential leaving enough space above the tubes for the plants to grow. Pot were placed under constant illumination supplied by 10 white, 40-watt, 120 cm long fluorescent lamps (approximately 5000 lux), at desired temperatures.

After 8 days, or as desired by the experiment, tubes were removed from the pots. After the unseeded half of a tube was carefully lifted, the roots in he seeded half, starting from the crown, were excised in 1 cm segments with a sterile scalpel. The scalpel was flamed between cuts. After loosely adhering soil was shaken off root segments with their adhering rhizosphere soil were air dried under a 100-watt lamp for 30 minutes. Each unit was weighed and transferred to a 20 ml glass vial containing 1 ml sterile distilled water. The contents of the vial were stirred vigorously with a sterile spatula. The colony forming units (cfu) of Trichoderma contained in the rhizosphere soil at each cm of root were determined by plating a series of 10-fold dilutions from the vial of Trichoderma-selective medium. Root segments were removed from the dilution flask, blotted on paper towel and weighed to determine the dry weight of rhizosphere soil removed through washing. In experiments where sand was substituted for soil and glass beads were coated with conidia, what would have been rhizosphere sand was sampled after 8 days and treated as explained above. Plates were incubated at 25° C. for 5 days. Counts of Trichoderma cfu per mg rhizosphere soil for each root segment were made with six replicates per treatment. All experiments were repeated twice.

Microscopic observation of roots. Root segments with rhizosphere soil were placed in multi-well tissue culture plates. One-half ml of an aqueous 0.3% Calcofluor solution (Calcofluor white M2R, Polysciences, Inc., Warrington, Pa.) was added to each well. The plate was covered with aluminum foil and incubated at 25° C. for 20 hours. Root segments were transferred to a microscope slide. After addition of a drop of water and a cover slip, the slide was viewed with an Olympus BH microscope (Olympus Optical Co., Tokyo, Japan), with a blue exciter filter (8G-12) providing 400 nm light supplied by an epifluorescent illuminator. A barrier filter (530 nm) also was used when viewing the slides. Each root segment was viewed and the total length of hyphae per root cm was measured with the aid of an ocular micrometer. The experiment was repeated twice.

Statistical analysis. The date for weight of mycelium and cellulase units produced was subjected to one way analysis of variance and the means were separated with an FLSD (P-32 0.05). The date of CSA were subjected to multiple regression analysis and the slopes values were separated with an FLSD (P=0.05).

MATERIALS

Soil. Nunn sandy loam was used in these investigations. Water content of 43.2 kg portions was adjusted to $-0.03$ bars and the soil was stored for 48 hours before use. The soils had the following characteristics: pH 7.0, conductivity 0.4 mmhos, lime low, organic matter 1.4%, $No_{3-N}$ 1 hg/g, P 9 hg/g, K 198 hg/g, Zn 0.5 hg/g, Fe 3.2 hg/g. Its pH was measured by the $CaCl_2$ method. To adjust soil pH, 10% (v/w) 0.1N $H_2SO_4$ was added to a 1 kg portion of soil. The soil was mixed thoroughly, allowed to dry, and ground with a mortar and pestel. By this method, soil pH was reduced from 7.0 to 2.5. Portions of this soil were added to field soil to adjust pH values from 7.0 to 5.0 and 6.0. No change in pH was observed during the course of experiments.

Trichoderma spp. and strains. Various strains of *Trichoderma harzianum* (e.g., T-95 [ATCC 60850] T-12B, WT, and T-12) and one strain each of *Trichoderma koningii* (T-8) and *Trichoderma viride* (T-S-1) were used in these investigations. They were obtained from various sources. For example, the *T. harzianum* designated as WT originally was isolated from a soil in Columbia, SA. *T. harzianum* (T-95) a benomyl tolerant mutant, was derived from *T. harzianum* WT. *T. harzianum* (T-12) *T. koningii* (T-8) were isolated from a soil in New York, were provided by G. E. Harman (New York State Agricultural Experiment Station, Geneva, N.Y.). *T. viride* (T-S-1) was provided by M. T. Dunn (Mycogen Corporation, San Diego, Calif.). *T. harzianum* (T-12B) was a benomyl tolerant mutant derived from *T. harzianum* (T-12). Conidia of the strain being tested were exposed to 100 μg/ml of N-methyl-N-nitro-N-nitrosoguanidine (Tredom Chemical, Inc., 255 Oser Ave., Hauppauge, N.Y.) for 30 minutes. The conidia were centrifuged at 2500 g for 15 minutes and resuspended in sterile water three times. Seeds of cucumber (*Cucumis sativus* L. "Straight Eight"), radish (*Raphanus sativus* L. "Early Scarlet Globe"), tomato (*Lycopersicum esculentum* L. Burpee's Big Boy), beans, (*Phaseolus vulgaris* L. "Olathe"), and maize (*Zea mays* L. T. E. 6998) were surface disinfested for 10 minutes in 1.1% sodium hypochlorite solution and 5% ethanol, washed in distilled water, and air dried. Seeds were treated with conidial suspensions of Trichoderma spp. in water containing 2% (v/w) Pelgel (The Nitragen Co., Milwaukee, Wis.) as a spreader or sticker. Conidial density was adjusted to 106 per seed. Controls were treated with Pelgel alone.

Competitive saprophytic ability assay. To test CSA of Trichoderma spp., the Cambridge method was modified. Strains of Trichoderma spp. were grown on potato-dextrose agar (PDA). Mutants tolerant to benomyl were grown on PDA containing 10 ug a.i. benomyl per ml. Plates were incubated for 8 days at 25° C., flooded with sterile distilled water and conidia were gently freed from the culture with a brush. The suspension was sieved through four layers of cheese cloth, centrifuged at 2500 grams for 15 minutes and resuspended in sterile distilled water three times. Conidia were counted with a hemacytometer and then adjusted to the desired concentrations.

Freshly harvested conidia were added to 7.2 kg of previously moistened and incubated field soil at the rate of 101, 102, 103 and 104 conidia per grams soil. No conidia were added in controls. The soil was mixed thoroughly by hand and distributed in nine 11-cm-diameter plastic pots.

Clean, mature, polished winter wheat straw was cut in 1-cm segments; each segment included a node. Twenty pieces were buried randomly in each pot. The pots were arranged in a completely randomized design, covered with plastic to conserve moisture at −0.03 bars and incubated in the dark. No water was added to the pots. All twenty pieces, from each treatment including a non-infested control were removed from the pots after 2, 4, or 6 days; washed in tap water to remove all adhering soil and debris and surface-disinfested in a mixture of 1.1% sodium hypochlorite solution and 5% ethanol for 5 minutes. Segments were plated on medium selective for Trichoderma and incubated at 25° C. for 5 days. Percent colonization of wheat pieces by Trichoderma for each treatment at a given time was determined. There were three replicates per treatment and all experiments were repeated twice.

In experiments where cellophane disks were substituted for straw pieces, the disks were obtained by punching holes (6-mm diameter) in an untreated cellophane sheet. Disks were removed from the pots after incubation for 2, 4, or 6 days, washed in sterile distilled water and plated on Trichoderma selective medium.

Growth of Trichoderma spp. in liquid culture. Strains of Trichoderma spp. were grown in 250 ml Erlenmeyer flasks containing 50 ml Czapek Dox broth on a rotary shaker at 100 rpm at 26° C. for 6 days. Finely ground cotton linters, carboxy methyl cellulose or cellobiose (Sigma Chemical Co., St. Louis, Mo.) were used as sole sources of carbon. Each flask was seeded with a 4-mm diameter disk of PDA on which the strains had been grown for 2 days. After 6 days the hyphal mat was removed aseptically and dried for 2 days at 60° C. to obtain the weight of mycelium. There were six replicates per strain.

Enzyme assay. Cellulase (E.C. 3.2.1.4) was assayed spectrophotometrically (A 340) by following the release of free glucose from the substrates listed above according to the manufacturer's directions (Sigma Chemical Co., St. Louis, Mo.). Cellulase activity was expressed as units of cellulase produced per ml culture filtrate of each strain when grown in the substrate for 6 days. There were six replicates per strain.

Competitive saprophytic ability (CSA) index. A CSA index for each strain was developed as follows:

$$CSA \text{ index } \sum_{n}^{i=1} = [\ln (l/1 - C_i)/(ti)(logpi)]/n \quad (1)$$

where c is the frequency of isolation of a specific strain of Trichoderma from the segments, t is time of incubation, p is the population density of conidia added to the soil and n is the number of treatments.

Rhizosphere competence (RC) index. Rhizosphere competence index (RC index) for each strain was developed from the data reported in reference 2 by use of the equation:

$$RC \text{ index } \sum_{n}^{i=1} = [\log(p_i + 1) \cdot \ln(d_i * 1)]/n \quad (2)$$

where p is the population density per mg rhizosphere soil, d is the root depth and n is the total root length.

EXPERIMENTAL RESULTS

Figure 1A:
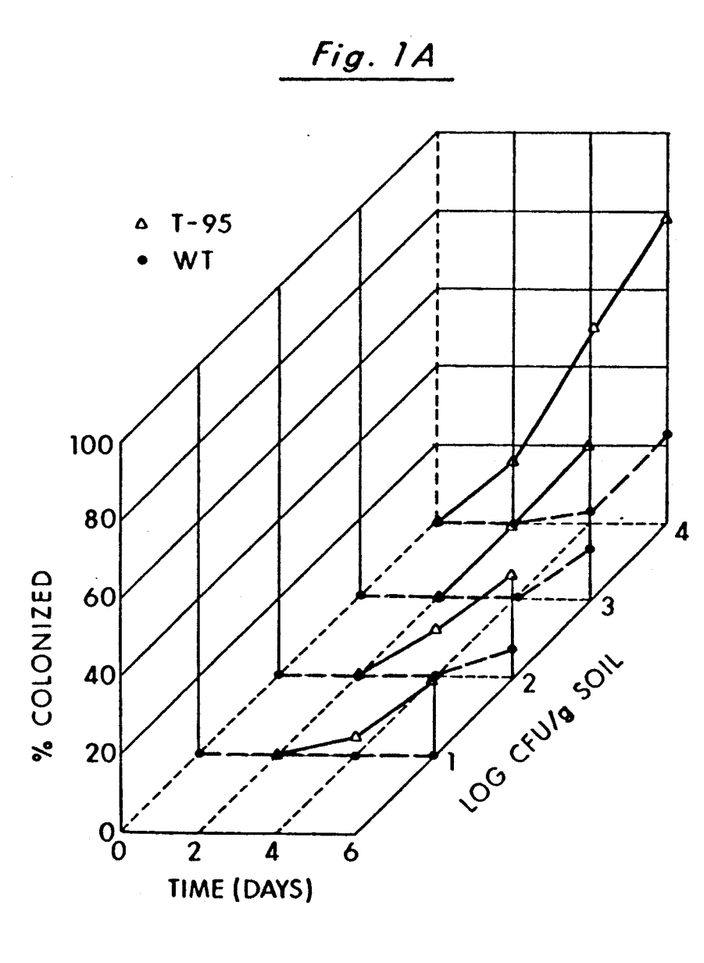
FIG. 1 depicts percent colonization of wheat straw segments by strains of Trichoderma harzianum.
Figure 1B:
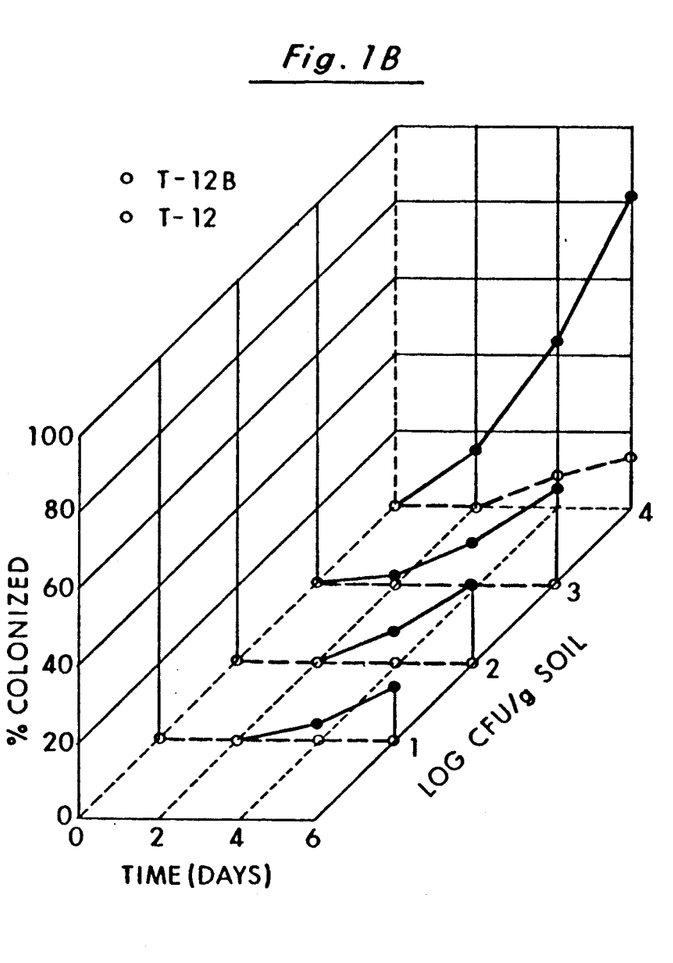

Colonization of straw by Trichoderma spp. When polished wheat straw pieces were buried in soil infested with conidia of Trichoderma spp. and removed after 2, 4, and 6 days, T. koningii (T-8) and T. viride (T-S-1) were not isolated at any population density. T. harzianum T-12 and WT were recovered from straw less frequently than the other strains and were slow to colonize the straw segments at higher population densities (FIG. 1). However, the mutants of these wild types, T-12B and T-95, respectively, were isolated from the straw segments at any population density (FIG. 1). Strains T-95 and T-12B showed significantly higher percent colonization than WT and T-12 at any population density on all days. Strain T-95 showed significantly higher percent colonization than T-12B at 101, 102, and 103 cfu/grams soil on all days but there were no significant differences between the two strains at 104 cfu/g. Strain WT showed significantly higher percent colonization than T-12 and WT were added at 101 cfu/grams soil, and 10⁴ cfu/g. When strains T-12 and WT were added at 10¹ cfu/grams soil, neither were isolated from what straw pieces after 2, 4, and 6 days incubation. Trichoderma spp. were not isolated from controls.

Figure 2:
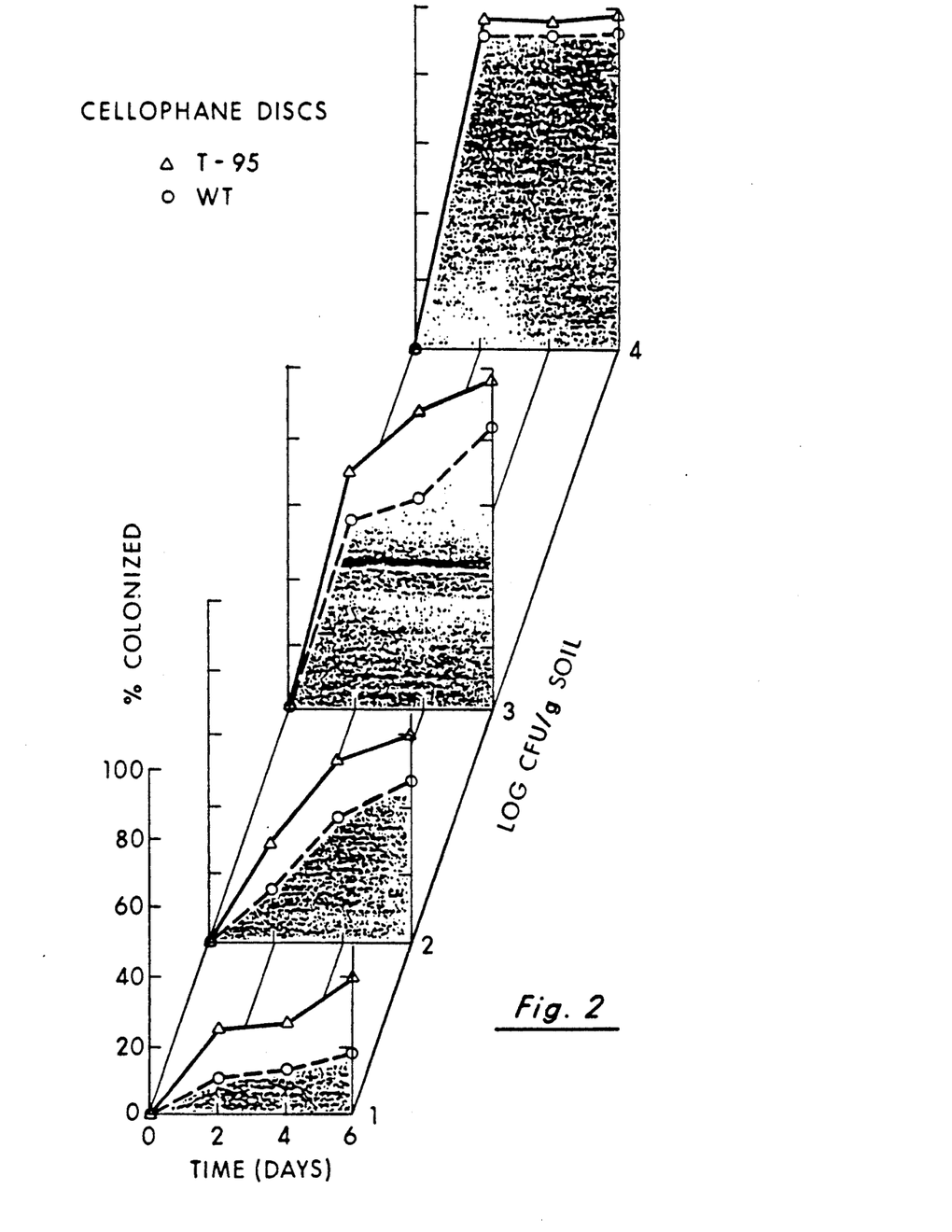
FIG. 2 depicts percent colonization of cellophane disks by two strains of Trichoderma harzianum.

When washed cellophane disks were buried in soil infested with conidia of T-95 or WT and removed after 2, 4, and 6 days, both strains could be isolated from the disks at any population density (FIG. 2). Strain T-95 showed significantly higher percent colonization than WT at 101, 102, and 103 cfu/grams soil on all days but there were no significant differences between the two strains at 104 cfu/g.

Figure 3A:
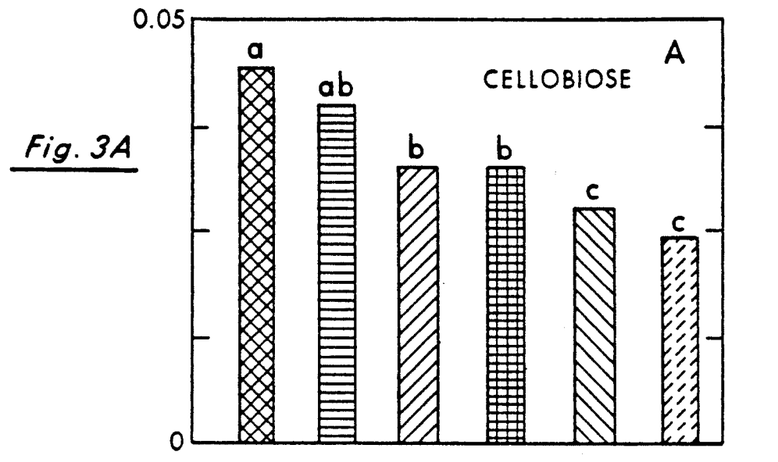
FIG. 3 is a bar graph depiction of the dry weight of mycelium of strains of Trichoderma spp. grown for 6 days in Czapek Dox broth with A., cellobiose, B., carboxy methyl cellulose (CMC), and C., cotton linters as the sole sources of carbon.
Figure 3B:
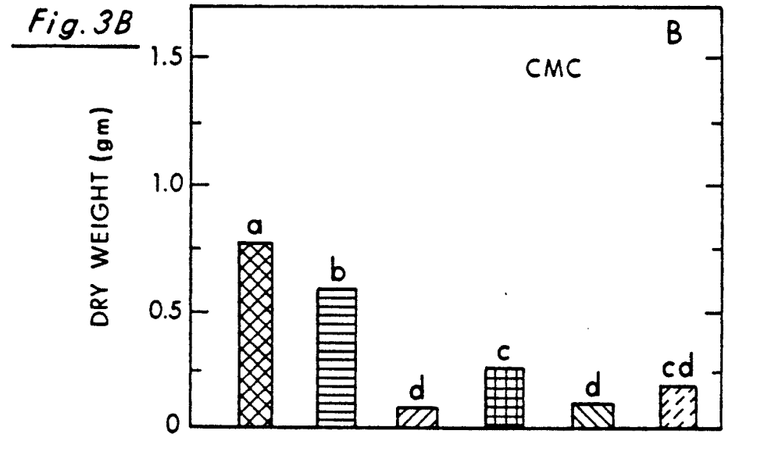
Figure 3C:
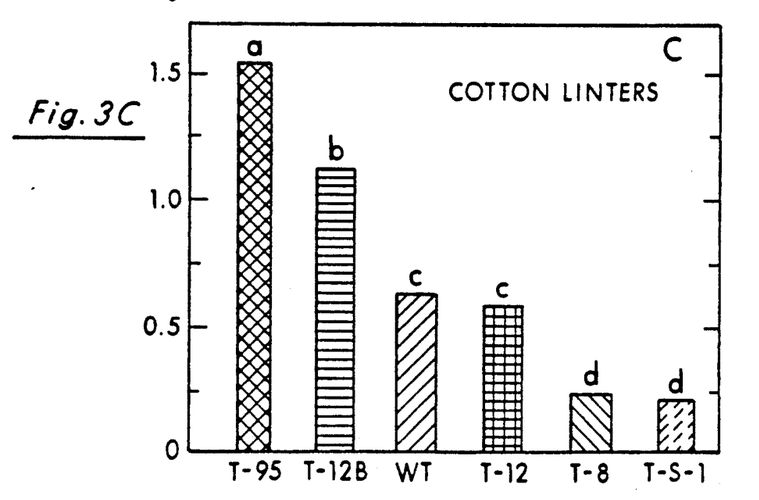

Growth of Trichoderma spp. in liquid culture. When strains of Trichoderma spp. were grown in Czapek Dox broth with cellobiose as the sole source of carbon, the mutant (T-95) mycelium attained significantly higher dry weight than all other wild type strains (FIG. 3A). Strains T-12B, T-12, and WT had significantly higher dry weight than T-8 and T-S-1. When carboxyl methyl cellulose or cotton linters were the sole source of carbon, the mutants T-95 and T-12B had significantly higher dry weights than the wild types (FIG. 3B and C). In both cases strain T-95 had significantly higher dry weight than T-12B. With cotton linters strains WT and T-12 had significantly higher dry weights than T-8 and T-S-1.

Figure 4A:
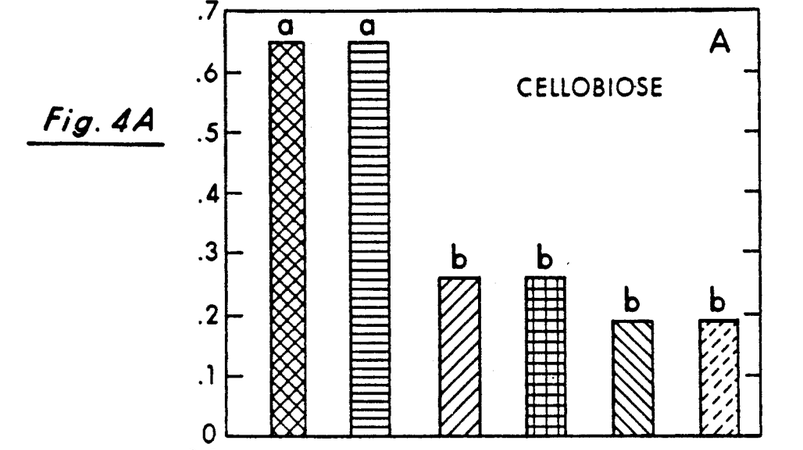
FIG. 4 shows cellulase activity of strains of Trichoderma spp. A., cellobiose, B., carboxy methyl cellulose (CMC), and C., cotton liners were the sole source of carbon.
Figure 4B:
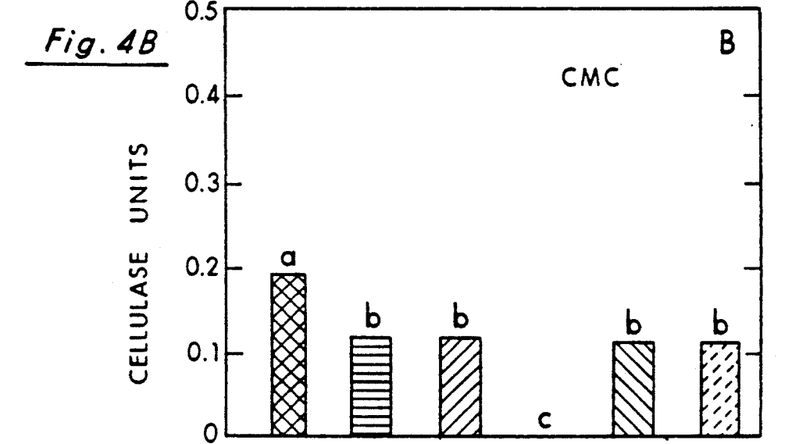
Figure 4C:
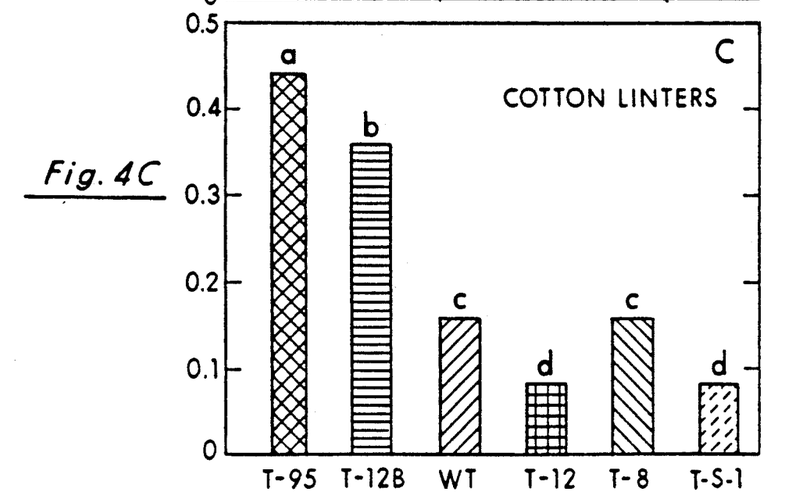
Figure 5:
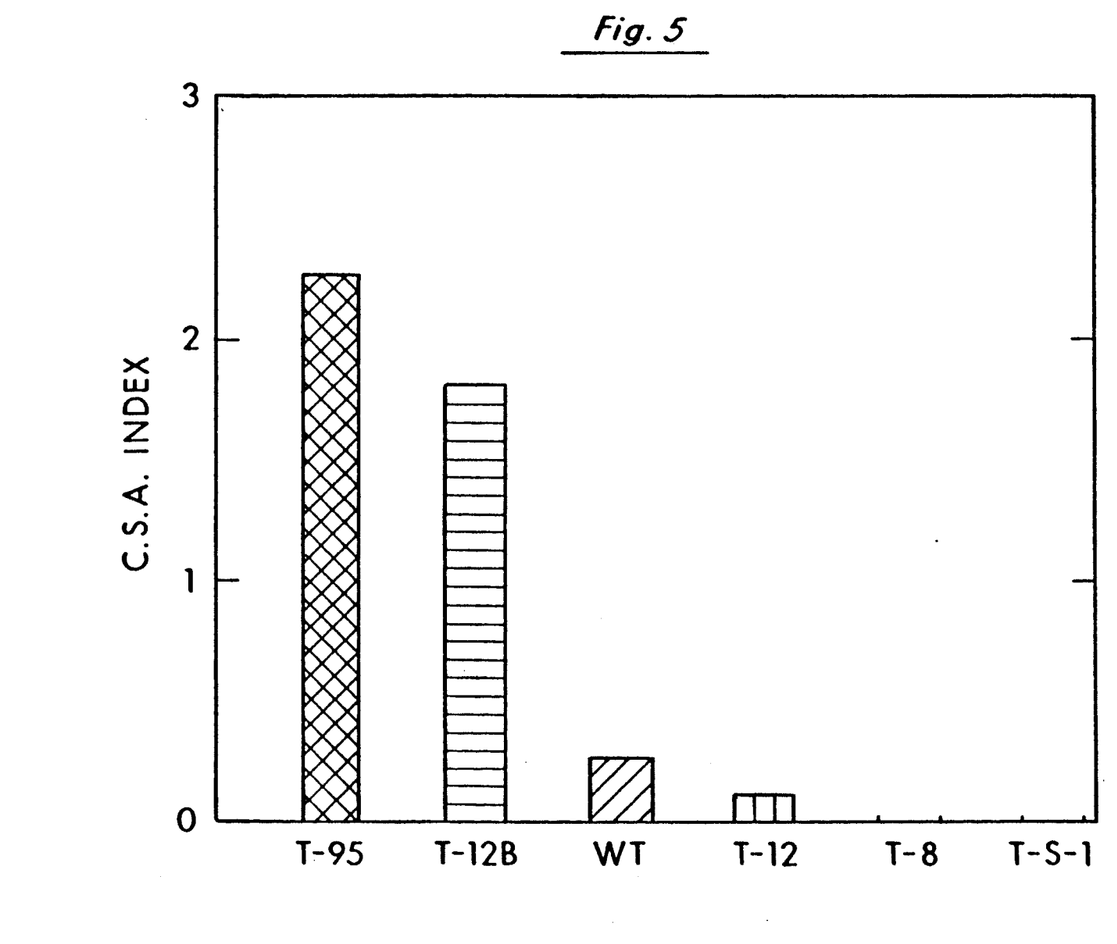
FIG. 5 is a bar graph depiction of competitive saprophytic ability (CSA) index of Trichoderma spp. and strains.

Production of Cellulase. All strains produced cellulase when grown in Czapek Dox broth with cellobiose as the sole source of carbon (FIG. 4A). Mutants T-95 and T-12B produced significantly higher amounts of cellulase than the wild type or other strains. When carboxy methyl cellulose was the sole source of carbon, strain T-12 failed to produce any cellulase, strain T-95 produced significantly higher amounts of cellulase than all other strains and mutant T-12B produced significantly more than T-12 (FIG. 4B). When cotton linters were the sole source of carbon, the mutants of T. harzianum produced significantly higher amounts of cellulase than the wild types or other strains and strain T-95 produced significantly higher amount than all other strains (FIG. 4C).

DISCUSSION

Isolation of fungi from baits of dead plant material buried in field soil provides direct evidence that recovered fungi can colonize these substrates as competitive saprophytes. Therefore, many investigators have used wheat straw pieces rich in cellulose in the Cambridge method to determine the competitive saprophytic ability of root infecting fungi. The CSA index measured the capacity of different strains and species of Trichoderma to compete effectively in the colonization of wheat straw. Benomyl-tolerant mutants had higher CSA indices than the wild types. Garret has included the ability to produce enzymes for utilization of specific substrates among the attributes of fungal species that contribute to their CSA.

Figure 6A:
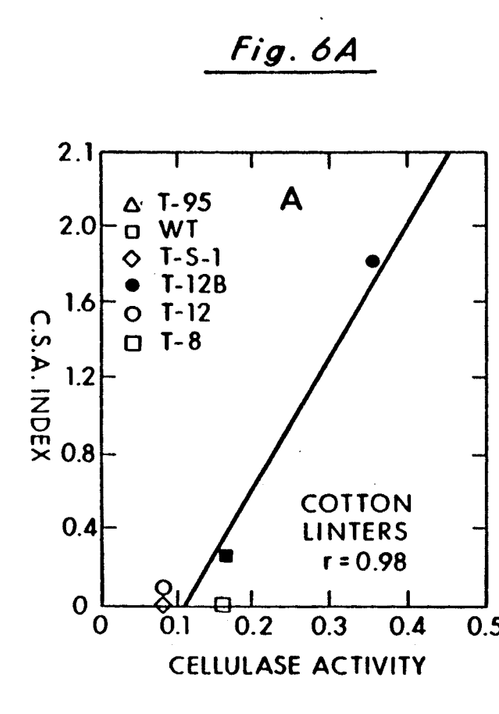
FIG. 6 shows the relation of competitive saprophytic ability (CSA) index of Trichoderma spp. and strains to the cellulase activity, B., rhizosphere competence (RC) index of Trichoderma spp. and strains to the cellulase activity when cotton liners were the sole source of carbon, and C., rhizosphere competence (RC) index to competitive saprophytic ability (CSA) index of Trichoderma spp. and strains.
Figure 6B:
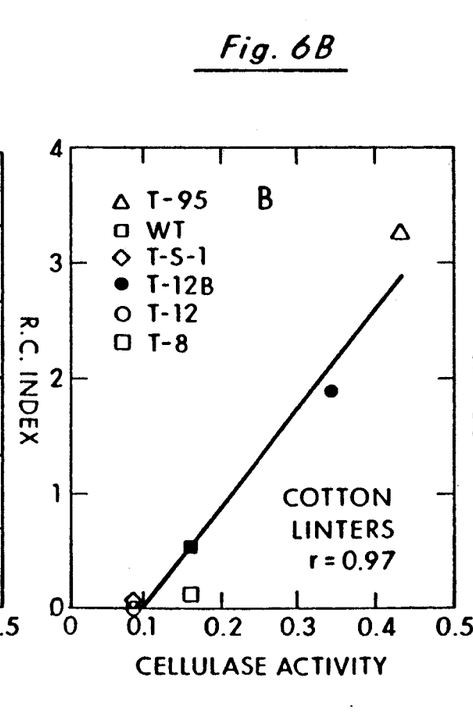
Figure 6C:
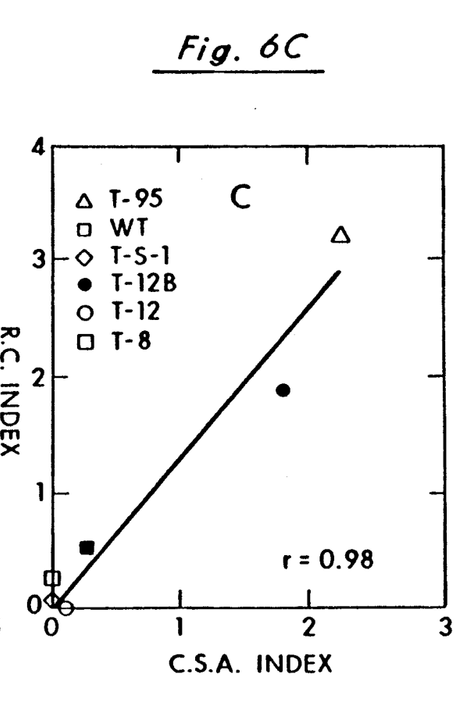

Strains of Trichoderma spp. produce cellulase and other cell wall degrading enzymes. In our study the CSA indices were correlated directly with production of cellulase (FIG. 6A). Also, mutants of *T. harzianum* produced significantly greater amounts of cellulase when (cotton linters) was the sole source of carbon. By use of the RC index, rhizosphere competence was directly correlated with amount of cellulase units produced by the mutants and the CSA of the mutants. These correlations indicate that mutants with higher cellulase activity than wild types can utilize cellulose substrates on or near the root more efficiently and thus, are rhizosphere-competent. Utilization of cellulose substrates is not associated with parasitism since microscopic examination revealed no evidence of such a relationship. A more likely source of cellulose substrates is the remains of the primary cell walls in the mucigel.

The pattern of hydrolytic enzymes used by strains of Trichoderma spp. for the hydrolysis of cellulose has been well studied. Exo and endo B-1,4-glucanases act on cellulose that is broken down to cellobiose and glucose. Cellobiose is further hydrolized by, B-1,4-glucosidases to glucose. In an attempt to distinguish the amount of these enzymes produced, different carbon sources were used as substrates. When cellobiose was used as the sole carbon source, the mutants produced significantly greater amount of B-1,4-glucosidases than the wild types. The mutants not only produced greater amounts of B-1,4-glucanases but, evidently, also produced significantly greater amounts of B-1,4-glucosidases and utilized the substrates more efficiently. This is also evident from the dry weight of mycelium produced.

These results indicate that certain strains of *T. Harzianum* are rhizosphere-competent because of increased enzyme activity which results in higher CSA for possession of cellulose substrates on or near the root surface. This attribute of rhizosphere-competence has not been previously recognized. If the extension rate of fungal thalli are sufficient to keep pace with root growth, the attribute of higher efficiency of cellulose degradation could be a key factor for inducing these microorganisms to become rhizosphere-competent.

These results also indicate that mutation and selection of other strains of other fungi and bacteria based upon an ability to produce rhizosphere competence in a wide variety of biocontrol agents.

Thus having disclosed our invention we claim:

1. A rhizosphere competent biocontrol agent, said biocontrol agent comprising *Trichoderma harzianum* ATCC 20835.

* * * * *